US00PP30067P3

(12) United States Plant Patent
Koie et al.

(10) Patent No.: US PP30,067 P3
(45) Date of Patent: Jan. 8, 2019

(54) HOP PLANT NAMED 'FURANO K906901060 GO'

(50) Latin Name: ***Humulus lupulus* L.**
Varietal Denomination: Furano K906901060 Go

(71) Applicant: Sapporo Breweries Limited, Tokyo (JP)

(72) Inventors: Koichiro Koie, Hokkaido (JP); Narushi Suda, Hokkaido (JP); Yutaka Itoga, Hokkaido (JP); Mitsuhiro Uemoto, Hokkaido (JP); Yasunori Arai, Hokkaido (JP); Masanobu Goto, Hokkaido (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 15/731,660

(22) Filed: Jul. 13, 2017

(65) Prior Publication Data

US 2018/0098474 P1 Apr. 5, 2018

(30) Foreign Application Priority Data

Oct. 5, 2016 (JP) ..... PBR 31508

(51) Int. Cl.
*A01H 5/02* (2018.01)

(52) U.S. Cl.
USPC ..... Plt./236
CPC ..... *A01H 5/02* (2013.01)

(58) Field of Classification Search
USPC ..... Plt./236
See application file for complete search history.

*Primary Examiner* — Susan McCormick Ewoldt
(74) *Attorney, Agent, or Firm* — Bethany R. Roahrig; James M. Weatherly; Cochran Freund & Young LLC

(57) ABSTRACT

A new hop plant particularly distinguished by having a cylindrical plant shape, large bracts, and a fruity, tropical fruit flavor, is disclosed.

2 Drawing Sheets

Genus and species: *Humulus lupulus* L.
Variety denomination: 'Furano K906901060 Go'.

CROSS REFERENCE TO RELATED APPLICATION

The present application claims priority to Japan Plant Variety Protection Application No. 31508, as filed on Oct. 5, 2016, the entire contents are herein incorporated by reference for all the application teaches and discloses.

BACKGROUND OF THE NEW PLANT

The present invention comprises a new and distinct variety of hop, botanically known as *Humulus lupulus* L. and hereinafter referred to by the variety name 'Furano K906901060 Go'. 'Furano K906901060 Go' is a selection from a controlled cross-pollination conducted in Kamifurano, Hokkaido, Japan between the proprietary female hop variety 'K843502179' and the male hop variety 'Saaz' (not patented) in 1990.

The seeds from the cross-pollination were sown in 1991 and plants were grown for evaluation. A plant line was selected in March, 2014 in Kamifurano, Hokkaido, Japan and named 'Furano K906901060 Go'. In 2014, 'Furano K906901060 Go' was first vegetatively propagated in Kamifurano, Hokkaido, Japan via vegetative cuttings. 'Furano K906901060 Go' was found to reproduce true to type in successive generations of asexual propagation via vegetative cuttings in Kamifurano, Hokkaido, Japan.

SUMMARY

The following are the most outstanding and distinguishing characteristics of this new variety when grown under normal horticultural practices in Kamifurano, Hokkaido, Japan.

1. Cylindrical plant shape;
2. Large bracts; and
3. A fruity, tropical fruity flavor.

DESCRIPTION OF THE PHOTOGRAPHS

This hop plant is illustrated by the accompanying photographs, which show the plant's overall plant shape, leaf shape and cone shape. The photographs are of three-year-old plants grown in Kamifurano, Hokkaido, Japan in August 2016. The colors shown are as true as can be reasonably obtained by conventional photographic procedures.

DESCRIPTION OF THE NEW VARIETY

Figure 1:
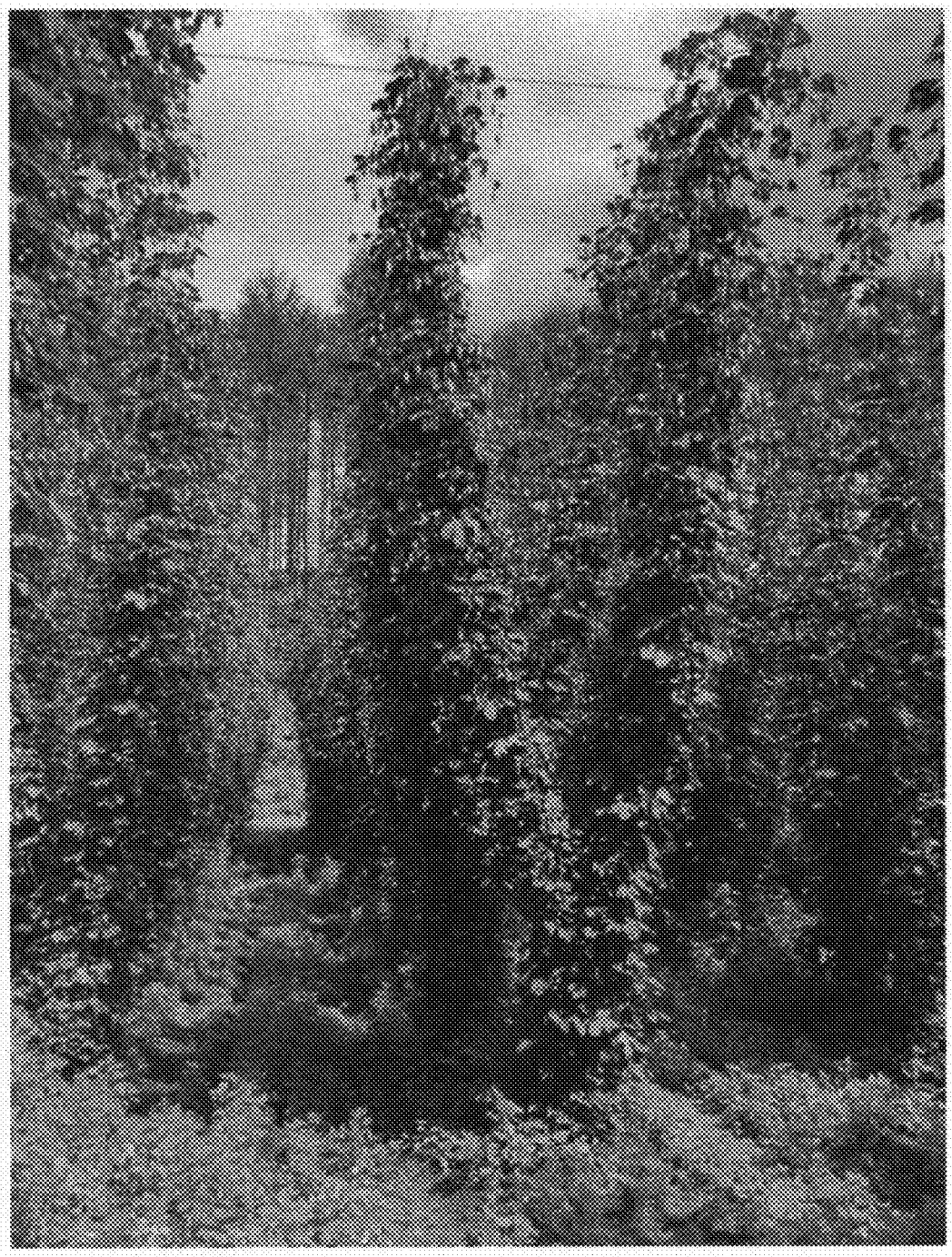
FIG. 1 shows the plant shape of 'Furano K906901060 Go'.
Figure 2:
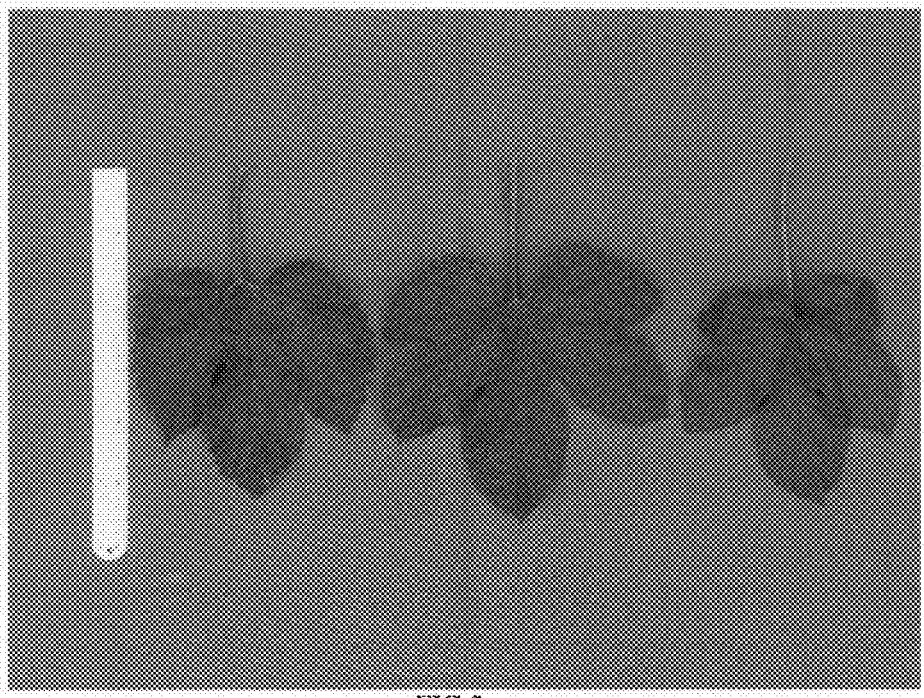
FIG. 2 shows the leaf shape of 'Furano K906901060 Go' (left) and two commercial varieties in Japan. In the middle is 'Little Star', and on the right is 'Furano Special'.
Figure 3:
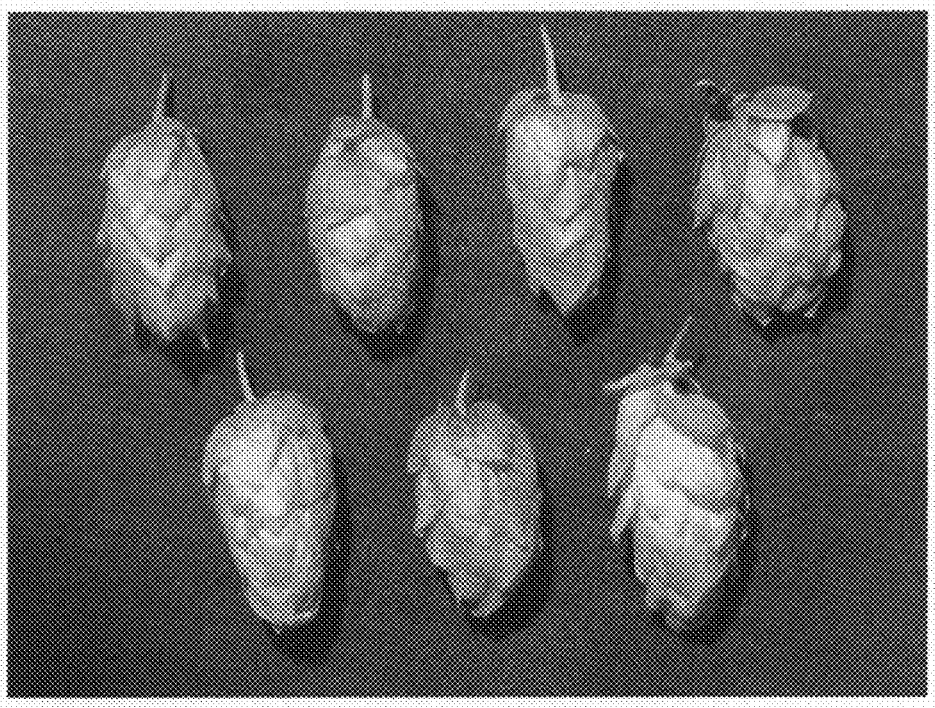
FIG. 3 shows the cone shape of 'Furano K906901060 Go'.

The following detailed descriptions set forth the distinctive characteristics of 'Furano K906901060 Go'. The data, which define these characteristics, were collected from asexual reproductions carried out in Kamifurano, Hokkaido, Japan. Data was collected on mature plants, aged between three and five years in Kamifurano, Hokkaido, Japan. Color references are to Japan Horticultural Plant Color Chart (1987, Japan Color Research Institute).

Classification:

*Family*.—Cannabaceae.

*Classification*.—*Humulus lupulus* L.

*Common name*.—Hop.

Propagation:

*Type*.—Vegetative cuttings.

Plant description:

*Plant and growth habit*.—The plant growth type is normal, not dwarf.

*Plant shape*.—Cylindrical.

*Plant height*.—5.5 m when grown on a trellis.

Lateral branch description:

*Length*.—Average of 0.53 m.

*Internode length*.—14.9 cm.

Foliage description:

*Arrangement*.—Opposite.

*Shape*.—Most leaves are palmate with three lobes, however heart shaped leaves are occasionally observed.

*Length*.—Average is 16.2 cm (2 year mean).

*Color, upper surface of fully expanded leaves*.—Deep yellowish green (Japan Color Chart No. 3706).

*The number of lobes*.—Three to five.

*Apex*.—Caudate.

*Base*.—Cordate.

*Margin*.—Serrate.

*Venation pattern*.—Palmate.

*Blistering*.—Upper surface: Weak to medium.

*Petiole*.—Length: Average is 7.5 cm; ranges between 6.5 cm and 8.5 cm. Diameter: Average is 3.8 mm; ranges between 3.0 mm and 5.0 mm measured in the middle. Color: From base to bine is a dark grey red (Japan Color Chart No. 0420).

Inflorescence buds:

*Cone size*.—Medium.

*Cone length*.—39.8 mm; ranges between 27.0 mm and 47.0 mm.

*Cone diameter*.—Average is 18.0 mm; ranges between 16.0 mm and 20.0 mm.

*Cone shape*.—Ovate.

*Weight of one hundred cones*.—Medium (21.3 g in dry matter).

*Color*.—Bright yellowish green (Japan Color Chart No. 3704).

*Flowering season*.—Early, around July 5$^{th}$.

Spike bracts:

*Length*.—Large (20.3 mm); ranges between 15.0 mm and 26.5 mm.

*Width*.—10.7 mm; ranges between 8.5 mm and 13.5 mm.

*Shape*.—Aristate.

*Margin*.—Entire.

*Color*.—Bright yellow green (Japan Color Chart No. 3704).

Bracteoles:

*Shape*.—Ovate.

*Length*.—Average is 14.7 mm; ranges between 13.5 mm and 16.5 mm.

*Width*.—Average is 8.6 mm; ranges between 7.0 mm and 10.5 mm.

*Apex*.—Round.

*Margin*.—Entire.

*Color*.—Light yellow green (Japan Color Chart No. 3703).

Bines:

*Color*.—The color of the ridge lines are a vivid purple (Japan Color Chart No. 8605) and the color of the area in-between is dull yellow green (Japan Color Chart No. 3513).

*Anthocyanin coloration*.—Medium.

*Diameter*.—Average is 8.8 mm; ranges between 7.0 mm and 11.0 mm.

*Internode length*.—Average is 25.0 cm; ranges between 21.5 cm and 30.0 cm at the height of 1.5 m.

*Stipule direction*.—Horizontal.

*Stipule color*.—Bright yellow green (Japan Color Chart No. 3504).

Pedicels: Not observed.

Reproductive organs:

*Stamens*.—Not observed.

*Pistils*.—Not observed.

Disease and pest/insect resistance: Field resistant against hop downy mildew. Not resistant to hop powdery mildew.

Brewing characteristics (2015): Content of alpha acid is 4.1% (moisture content is adjusted to 11%). Content of beta acid is 6.2% (moisture content is adjusted to 11%). Ratio content of beta acids to alpha acids is 1.5. Content of humulene is 22.2%. Content of caryophyllene is 20.6%. Ratio content of humulene to caryophyllene is 1.08. Content of myrcene is 51.8%. Content of farnesene is 0.3%. Content of linalool is 2.7%. Ratio of co-alpha to all alpha acids is 15%. Flavor of 'Furano K906901060 Go' is fruity, such as mango or tropical fruits.

*Storage stability*.—75.4% after 6 months at room temperature.

Yield: 1.36 tons per hectare.

COMPARISON WITH PARENTAL LINES AND KNOWN VARIETY

'Furano K90601060 Go' is a distinct variety of hop. The female parental line of 'Furano K90601060 Go' no longer exists. However, 'Furano K90601060 Go' can be distinguished from its maternal grandmother, 'Atlas' as described in Table 1:

TABLE 1

Comparison with Parental Lines

| Characteristic | Variety 'Furano K90601060 Go' | Maternal grandmother 'Atlas' |
|---|---|---|
| Leaf shape | 3 lobes | 5 lobes |
| Color of stem | 6 red stripes along the bine axis direction with green intermediate area | Stripes have no distinctive color compared to green intermediate area between stripes |
| Alpha acids (%) | 4.1% | 6.4% |
| Content of cohumulone in alpha acids (%) | 15% | 40% |
| Beta acids (%) | 6.2% | 2.9% |
| Ratio of beta acids to alpha acids | 1.5 | 2.3 |

'Furano K90601060 Go' is distinguished from its male parent 'Saaz' in that 'Furano K90601060 Go' develops female flowers that develop into mature hop cones without producing pollen, whereas 'Saaz' produces pollen without developing into female flowers.

'Furano K90601060 Go' is distinguished from the commercial hop variety 'Hallertau Tradition'. Differences between the two varieties are described in Table 2:

TABLE 2

| Comparison with Similar Variety | | |
|---|---|---|
| Characteristic | Variety 'Furano K90601060 Go' | Commercial line 'Hallertau Tradition' |
| Flowering season | Jul. $5^{th}$ | Jul. $10^{th}$ |
| Content of alpha acid | 4.1% | 6.2% |
| Content of beta acid | 6.2% | 3.3% |

TABLE 2-continued

| Comparison with Similar Variety | | |
|---|---|---|
| Characteristic | Variety 'Furano K90601060 Go' | Commercial line 'Hallertau Tradition' |
| Ratio of co-alpha to all alpha acids | 15% | 20% |
| Ratio content of beta acids to alpha acids | 1.5% | 0.5% |

We claim:

1. A new and distinct variety of hop plant named 'Furano K906901060 Go' as illustrated and described herein.

* * * * *